United States Patent
Kief

(10) Patent No.: US 6,407,085 B1
(45) Date of Patent: *Jun. 18, 2002

(54) MEDICAMENT CONTAINING BETASITOSTEROL AND/OR PHYTOSTEROL/BETASITOSTEROL MIXTURES

(76) Inventor: Horst Kief, London Ring 105, D-67069, Ludwigshafen (DE)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/341,632
(22) PCT Filed: Jan. 16, 1998
(86) PCT No.: PCT/EP98/00227
§ 371 (c)(1), (2), (4) Date: Sep. 2, 1999
(87) PCT Pub. No.: WO98/31372
PCT Pub. Date: Jul. 23, 1998

(30) Foreign Application Priority Data

Jan. 16, 1997 (DE) .......................... 197 01 264

(51) Int. Cl.⁷ .............................. A61K 31/56
(52) U.S. Cl. ...................... 514/182; 514/863
(58) Field of Search .................. 514/567, 570, 514/170, 785, 182

(56) References Cited

U.S. PATENT DOCUMENTS

| 4,260,603 | A | | 4/1981 | Pegel et al. |
| 5,487,900 | A | * | 1/1996 | Itoh et al. |
| 5,574,063 | A | * | 11/1996 | Perricone .................... 514/474 |
| 5,709,868 | A | * | 1/1998 | Perricone .................... 424/401 |
| 5,965,618 | A | * | 10/1999 | Perricone .................... 514/558 |

FOREIGN PATENT DOCUMENTS

| DE | 35 46 360 A | 6/1987 |
| EP | 0 358 970 A | 3/1990 |
| EP | 0 509 656 A | 10/1992 |
| EP | 0 514 328 A | 11/1992 |
| EP | 645167 | * 3/1995 |
| EP | 0 203 277 A | 12/1996 |
| GB | 938 937 A | 10/1963 |
| GB | 2 238 476 A | 6/1991 |
| JP | 63 156 727 A | 6/1988 |
| JP | 02 025 425 A | 1/1990 |
| JP | 07 277 986 A | 10/1995 |
| JP | 07 304 684 A | 11/1995 |
| JP | 08 081 352 A | 3/1996 |
| JP | 08 104 632 A | 4/1996 |
| JP | 09 169 659 A | 6/1997 |
| RU | 2 069 557 C | 11/1996 |
| SU | 1 138 162 A | 2/1985 |

OTHER PUBLICATIONS

Antan et al., Spectrophotometric . . . , Khim.–Farm Zh., vol. 29/6, pp. 57–61, 1995.*
Marteau et al, Action of cholic and chenodeoxycholic . . . , Can. J. Physio. Pharmacol. vol. 58/9, pp. 1058–1062, 1980.*
Marugo et al., Effects of ursodeoxycholic acid . . . , IRCS Medical Science, vol. 7/10, pp. 531, 1979.*
Deschner et al, The influence of dietary . . . , Precancerous lesions Gastrointest. Tract.–1983, pp. 219–221, 1981.*

* cited by examiner

Primary Examiner—William R. A. Jarvis
Assistant Examiner—Vickie Kim
(74) Attorney, Agent, or Firm—Banner & Witcoff, Ltd.

(57) ABSTRACT

The invention relates to a medicament containing mixtures of betasitosterol and phytosterol and/or betasitosterol and its physiological metabolites. Processes were discovered for dissolving betasitosterol, which in itself is difficult to dissolve, in various oils and paraffins and in glycerin, which processes offer new indications for the use of these substances. In addition, the esterification of the betasitosterol with carboxylic acids opens up therapeutic possibilities in asthma, inflammatory intestinal diseases, arterial hypertension, autoimmune diseases of the skin and pain relief which far exceed the currently known range of uses of betasitosterol and phytosterol/betasitosterol mixtures.

3 Claims, No Drawings

MEDICAMENT CONTAINING BETASITOSTEROL AND/OR PHYTOSTEROL/BETASITOSTEROL MIXTURES

This application is 391 of PCT/EP98/00227 filed Jan. 16, 1998.

The object of the invention is a medicament which contains betasitosterol—phytoserol mixtures and/or betasitosterol and its physiological metabolites. Processes for dissolving betasitosterol, which in itself is difficult to dissolve, in various oils, paraffins, and glycerins were discovered which open new indications for the use of these substances. In addition, the esterification of betasitosterol with carboxylic acids opens up therapeutic possibilities for asthma, enflamed intestinal diseases, arterial hypertension, autoimmnune diseases of the skin, and for relieving pain which extend far beyond the currently known range for the use of betasitosterol and/or phytosterol/betasitosterol mixtures.

Naturally occurring phytosterols are usually a mixture of various sterols (e.g., campesterol, stigmasterol, among others), the most important component of which is the betasitosterol. For example, it can be derived as an extract from plants, including soy beans or saw palmetto berries by known methods. For decades it has been used in medicine with two indications:

1. As a medication for benign prostatic hyperplasia.
2. As a cholesterol resorption inhibitor.

The substance is practically nontoxic and interferes with the release of eicosanoic acid from biomembranes, as a result of which inflammation processes are retarded. A drawback is its insolubility; accordingly it attains a resorption quotient of only around 5% in healthy subjects. A further drawback is that at elevated doses, as it is used for lowering lipids, the resorption quotient and thus the systemic bioavailability drops drastically, i.e., almost no resorption takes place (saturation kinetic).

The use of betasitosterol is extremely low in side effects. Even in the case of oral administration of up to 24 g per day, a blood count of only 10 mg is reached due to the low resorption quotient. In the organism, it is 60% to 75% glucoronidated and around 20% is metabolized into cholic acid ($C_{23}H_{36}(OH)_3COOH$) and chenodesoxycholic acid ($C_{23}H_{37}(OH)_2COOH$). Cholic acid is further reduced by intestinal bacteria into desoxycholic acid.

The percutaneous use of betasitosterol and/or its physiologic metabolites in diseases of the skin and the subcutaneous tissue is unknown. In like manner, no areas of application are known for betasitosterol/phytosterol mixtures in oral administration other than the indications "benign prostatic hyperplasia" and "cholesterol resorption inhibition."

It is known that the resorption quotient, distributability, and excretion quotient, in short the pharmacokinetics of a preparation, are very strongly dependent not only on its chemical partners, but also on its physical solubility in various media.

The novelty according to the invention is comprised of esterifying phytosterols, in particular betasitosterol, primarily with carboxylic acids and dicarboxylic acids.

In addition, dissolving processes according to the invention for phytosterol/betasitosterol mixtures were found which make possible additional therapeutic uses, for example against diseases of the skin such as psoriasis and neurodermatitis. Lactic acid, ascorbic acid, gluconic acid, and tartaric acid are particularly advantageous for the esterifying due to their physiological effectiveness in the organism, their therapeutic reliability, and their lack of side effects.

The advantage of these compounds is to be found in the fact that with proper selection of the carboxylic acid, both reaction substances in themselves are nontoxic. In like manner, for example, the betasitosterol, ascorbic, and gluconic acid esters which are thereby generated are free of side effects and very well tolerated when taken orally.

For percutaneous use, the binding of phytosterol/betasitosterol mixtures to alcohols, but also to diols and triols, in the latter case the formation of a triglyceride is particularly suitable. Straight-chained primary alcohols, which have proven to be of value in skin care and therapy, are particularly suitable for this. betasitosterol (D'ans-Lax, 2-743: soluble in chloroform) which is soluble per se only with difficulty, dissolves in sufficient quantity in linseed oil, safflower oil, and so-called neutral oil if it is allowed to stand longer than 24 h, and very advantageously longer than 36 h at room temperature (neutral oil is a semisynthetic oil of medium-chain triglycerides). In neutral oil and in linseed oil, the solubility of desoxycholic acid corresponds approximately to that of betasitosterols. Desoxycholic acid in the form of its alkali salts and in particular its sodium salt in addition is relatively water soluble; through the addition of sodium desoxycholate, the solubility of betasitosterol in oil is further improved. Upon addition of desoxycholic acid, both oils become opalescent.

The solubility of phytosterol/betasitosterol mixtures and betasitosterol metabolites can be accelerated and improved with respect to yield if the effective ingredients are treated in oil, paraffins, stearates, or Vaseline with the application of heat at temperatures of around 70° C. to 160° C., advantageously at 120° C. to 140° C., advantageously over a period of 30 minutes to 3 hours.

If betasitosterol or sodium desoxycholate is heated in diverse natural and mineral oils, paraffins, commercially-available hypoallergenic stearate mixtures, or Vaseline (2 g substance in 100 ml) to 120° C., both substances dissolve fully within 90 minutes. Upon further heating to 150° C. (at 140° C., betasitosterol becomes liquid), betasitosterol dissolves up to around 15% in stearate mixtures, paraffins, and plant and mineral oils. After cooling, sodium desoxycholate remains clear dissolved in oil, while betasitosterol becomes slightly opalescent in oil. In like manner, betasitosterol and sodium desoxycholate can be introduced into glycerin. In this case, both substances dissolve completely clear upon being heated to 120° C. Upon cooling, the betasitosterol-glycerin solution is slightly opalescent, while again in this case sodium desoxycholate remains clear. Desoxycholic acid with safflower oil when heated to 120° C. yields a cloudy-opalescent emulsion; with glycerin following cooling it yields a white pasty mass which, however, after heating can easily be stirred into any salve base.

Microscopic monitoring of the opalescent phases shows that upon cooling, the solubility of the betasitosterol/phytosterol mixture drops, the dispersed phases partially separate, so that in part a suspension develops.

The solubility of phytosterol/betasitosterol mixtures and betasitosterol metabolites in oil, stearates, and glycerin under the described conditions without the assistance of emulsifying agents is of great therapeutic advantage, since the atopic skin easily becomes allergic and the potential danger of inducing an inflammation process is increased through a multiplicity of substances in a salve.

A special advantage of the betasitosterol-glycerin mixture is its water solubility. The ester of the betasitosterol with carboxylic acids, in particular with ascorbic acid or lactic acid, also becomes water soluble. The esterification of the betasitosterol with carboxylic acid also has the advantage that the excess amounts of carboxylic acid are relative acidic and thus as a salve component represent a valuable aid for maintaining the protective acidic coating of the skin. The esterification of carboxylic and dicarboxylic acids takes place according to known processes. In like manner, saturated, single and multiple unsaturated oleic acid esters, stearolic acid esters, and triglycerides can be formed according to the state of the art with acid catalysts using remaining unesterified portions.

Through the formation of betasitosterol-oleic acid or stearic acid esters on the one hand and glycerin-ascorbic acid and lactic acid esters on the other, it is possible to apply cortisone-like structures to the skin both in fat-soluble form as well as in water-soluble preparations and thus to ensure a very good diffusion through the upper layers of the skin.

If phytosterol/betasitosterol mixtures, when they are dissolved in the above described form in oil, are stirred into a salve base alone or in a mixture with sodium desoxycholate in aqueous solution in a concentration of 0.5 to 2.0% and the salve base is applied to the skin, the itching of neurodermatitis usually is eased after only 2 to 5 minutes. Inflammation processes with redness and swelling are alleviated after 24 to 48 hours. Thus a histamine antagonistic as well as a cortisone-like effect is determined, but without the side effects of the hormone. In the case of psoriasis, the formation of scales is often reduced even in extreme cases only 24 hours after the first application, particularly with the use of the metabolite desoxycholic acid. Here again the use of such substances is completely unproblematic in contrast to a salve with a component of vitamin-D-like structure, which as a result of the resorption of the vitamin-D-like molecule can be applied only to a limited extent because of the danger of overdosing and thus the influencing of calcium metabolism.

If betasitosterol or desoxycholic acid in the form of alkali desoxycholates, in particular of sodium desoxycholate or both substances together are applied in a resorbable salve or gel base to inflamed swellings or for arthrosis, arthritis, or soft-tissue rheumatism, a lasting reduction of pain and reduction of swelling of the inflamed area is achieved within 2 to 3 days.

While only prostatic hyperplasia and high cholesterol are known as indications for betasitosterol in oral administration, and despite knowledge of the prostaglandin inhibition, it has not been possible to find an additional indication in this regard, the combinations according to the invention of phytosterol/betasitosterol with (di-)carboxylic acids, in particular ascorbic acid administered orally have clear, significant effects which go well beyond the old indications.

1. One of the first steps in the triggering of pain is the emission of mediators of the prostaglandin cascade through the inflammation process. The substance acts in this regard promptly and limits pain both for patients with rheumatism as well as in those with malignant diseases.
2. Arterial hypertension is often triggered through inflammation processes at the kidneys. The substance acts as an antihypertensive agent upon this indication rapidly and without side effects or it intensifies the effect of specific antihypertensive agents.
3. Some atopic and autoimmune-induced skin diseases also take a pathophysiological "side road" through prostaglandin cascade. Here, too, clear improvements of the condition of the skin are achieved without side effects occurring.
4. Spasm of the smooth bronchial muscles in asthma bronchial is in most cases reduced within a few minutes. The substance group thus results in considerable reductions in applications of cortisone with its side effects.
5. Pain and inflammation processes in ulcerated colitis and Crohn's disease are reduced.

These indications are particularly applicable for esters of betasitosterol with ascorbic acid and lactic acid. The new substance group thus demonstrates a spectrum of effectiveness which extends far beyond that which these substances can claim individually.

What is claimed is:

1. A method of treating inflammation comprising administering a composition consisting essentially of an effective amount of betasitosterol ascorbic acid ester present in an amount of 0.5 to 2.0% by weight and a pharmaceutically acceptable carrier.

2. The method of claim 1 further comprising administering the composition by applying topically to inflammation of skin or subcutaneous tissue.

3. The method of claim 2 wherein the inflammation is neurodermatitis or psoriasis.

* * * * *